(12) United States Patent
Brackmann et al.

(10) Patent No.: US 6,714,837 B1
(45) Date of Patent: Mar. 30, 2004

(54) COUPON APPLICATOR AND METHODS OF APPLYING COUPON STRIPS TO GROCERY CARTS

(76) Inventors: Rogers F. Brackmann, 931 W. Liberty Dr., Wheaten, IL (US) 60187; Jacques M. Dulin, 4168 Thain Way, Palo Alto, CA (US) 94306

( * ) Notice: Subject to any disclaimer, the term of this patent is extended or adjusted under 35 U.S.C. 154(b) by 0 days.

(21) Appl. No.: 09/471,578

(22) Filed: Dec. 23, 1999

Related U.S. Application Data

(62) Division of application No. 09/215,903, filed on Dec. 18, 1998, now Pat. No. 6,090,218.
(60) Provisional application No. 60/068,600, filed on Dec. 22, 1997.

(51) Int. Cl.[7] .............................................. G06F 17/00
(52) U.S. Cl. ............................ 700/231; 705/14; 40/308
(58) Field of Search ................... 705/14, 1, 26, 705/27; 235/383, 385; 473/251; 709/228, 227, 229; 221/1, 9; 40/308, 661.12; 280/33.992; 224/41; 700/242, 231; 156/350, 384, 443, 538

(56) References Cited

U.S. PATENT DOCUMENTS

| 2,997,048 A | 8/1961 | Gertken et al. ............... 134/72 |
| 3,022,791 A | 2/1962 | Larson ......................... 134/70 |
| 3,096,775 A | 7/1963 | Clarke et al. ................ 134/123 |
| 3,148,820 A | 9/1964 | Robbins et al. ............... 229/37 |
| 3,179,117 A | 4/1965 | Gibson et al. ............... 134/107 |
| 3,218,748 A | * 11/1965 | Hopp ........................... 40/308 |
| 3,236,960 A | 2/1966 | Larson ..................... 200/61.41 |
| 3,258,019 A | 6/1966 | Bellas ......................... 134/99 |
| 3,289,238 A | 12/1966 | Sorenson et al. ............. 15/306 |
| 3,444,867 A | 5/1969 | Thornton ..................... 134/123 |
| 3,484,976 A | 12/1969 | Shea ........................... 40/310 |
| 3,561,391 A | 2/1971 | Locati ......................... 114/222 |
| 3,677,570 A | * 7/1972 | Hedu ........................ 280/33.99 |
| 3,698,029 A | 10/1972 | Pulliam ....................... 15/21 D |
| 3,995,555 A | 12/1976 | Stewart ....................... 101/426 |
| 4,039,181 A | 8/1977 | Prewer ......................... 271/10 |
| 4,268,344 A | 5/1981 | Jones .......................... 156/383 |
| 4,279,263 A | 7/1981 | Pulliam ....................... 134/111 |
| 4,345,393 A | 8/1982 | Price et al. ................... 40/312 |

(List continued on next page.)

FOREIGN PATENT DOCUMENTS

FR 2632285 * 12/1989
WO WO 96/30247 * 10/1996

OTHER PUBLICATIONS

No Author listed, "Messages Everyone can Handle", Grocery Marketing, v. 57, n. 6, p. 6(2), Jun. 24, 1991.*

*Primary Examiner*—M. Kemper
(74) *Attorney, Agent, or Firm*—Innovation Law Group, Ltd.; Jacques M. Dulin, Esq.

(57) ABSTRACT

An incentive-based grocery cart washing and disinfecting system including a consumer special-offer coupon applying apparatus, for use in a batch or continuous process comprising a housing having at least one pipe manifold with nozzles positioned therein to provide at least one treatment zone selected from pre-wash, wash, disinfecting, and rinse zones. In addition, blown air water-stripping/drying zones may be provided, with a heating source to assist drying. Following drying, a strip of specially adapted grocery coupons is optionally applied to the grocery cart handle, so that the coupons can be redeemed by customers during their subsequent shopping. The coupon strip comprises a leader portion and a coupon portion, and the leader can be wrapped and fixed around the grocery cart handle manually or by means of the automated machinery described. The system of the invention may be a fixed or mobile system, with the use preferably being on site at stores.

30 Claims, 4 Drawing Sheets

U.S. PATENT DOCUMENTS

| | | | |
|---|---|---|---|
| 4,512,504 A | 4/1985 | Owlett | 224/42.46 R |
| 4,562,848 A | 1/1986 | Messing et al. | 134/123 |
| 4,717,043 A | 1/1988 | Groover et al. | 221/7 |
| 4,807,319 A | 2/1989 | Poitevin | 15/21 D |
| 5,038,986 A | 8/1991 | Beauchesne | 224/277 |
| 5,072,956 A * | 12/1991 | Tannehill et al. | 280/33.992 |
| 5,079,901 A | 1/1992 | Kotsiopoulos | 53/435 |
| 5,102,168 A | 4/1992 | Gold | 283/105 |
| 5,106,124 A | 4/1992 | Volkman et al. | 283/81 |
| 5,133,375 A | 7/1992 | Schinzing et al. | 134/123 |
| 5,250,789 A * | 10/1993 | Johnsen | 235/383 |
| 5,271,634 A | 12/1993 | Walton | 280/33.992 |
| 5,285,802 A | 2/1994 | Soderquist | 134/123 |
| 5,287,266 A * | 2/1994 | Malec et al. | 364/401 |
| 5,305,935 A | 4/1994 | Weiner | 224/277 |
| D349,368 S | 8/1994 | Haskins | D32/4 |
| 5,360,094 A | 11/1994 | Adams et al. | 194/212 |
| 5,388,667 A | 2/1995 | Sonnendorfer et al. | 184/64 |
| 5,423,339 A | 6/1995 | Latimer | 134/104.2 |
| 5,427,392 A * | 6/1995 | Duer | 280/33.992 |
| 5,473,991 A | 12/1995 | Crum | 104/172.3 |
| D377,372 S | 1/1997 | Thompson | D19/1 |
| 5,622,196 A | 4/1997 | Luongo | 134/72 |
| 5,734,129 A * | 3/1998 | Belville et al. | 178/18 |
| 6,168,079 B1 * | 1/2001 | Becker et al. | 235/383 |

\* cited by examiner

COUPON APPLICATOR AND METHODS OF APPLYING COUPON STRIPS TO GROCERY CARTS

CROSS REFERENCE TO RELATED APPLICATION

Priority is claimed under 35 USC §119(e) to U.S. Provisional Application No. 60/068,600 filed Dec. 22, 1997 by the same inventors. This application is a Divisional of Ser. No. 09/215,903 filed Dec. 18, 1998 by the same inventors, titled "Incentive Coupon-Based System and Apparatus for Treating Grocery Carts", now U.S. Pat. No. 6,090,214, Issued Jul. 18, 2000, the priority of which is claimed under 35 USC §120.

TECHNICAL FIELD

This invention relates to incentive-based treatment systems for washing and disinfecting carts, and more particularly to automated or manual continuous or batch systems and methods for cleaning and disinfection treatment of grocery-type carts and preparing the carts for consumer service, including applying advertising attachments following the cleaning operation. The system includes a method and apparatus for applying one or more "cents-off" type of coupons to the handle of a grocery cart so that customers, upon entering the store, will receive special deal coupons at the moment of entering the store which they can redeem during their subsequent shopping as an incentive to stores to clean the carts. The cleaning system may be fixed or mobile, with the use preferably being on site at stores. The coupon apparatus may be used independently of the cleaning system.

BACKGROUND ART

Grocery-type carts are widely used, not only in groceries but also in a wide variety of retail stores, ranging from computer super stores to hardware stores. Indeed, such "purchase item" carts are so ubiquitous that they are typically the first item the consumer encounters, even before entering the particular store. As such, they are not only functional, but they are also an ambassador of the image and good will of the store.

Such carts are routinely abused by customers. Many have provision for toddlers or infant seats, and kids often ride in the lower shelf, hang off the sides, or sit or even stand in the basket. The customers and their children often have food which they spill, or they leave soiled diapers or other trash in or on the carts. Many are abandoned some distance from the stores and accumulate dirt and dust, gum, tar, and urine. Many of the children who ride in the carts are sick. As a result, many of these carts become increasingly filthy, and, in short, are disgusting for the consumer, as well as being a health hazard.

Current practice is for stores to occasionally hose them off. How well and often this is done is up to the store policy as carried out by its managers and staff assigned to that task. In some areas, such as the Northern States where the carts are also subject to winter salt, snow and grime, the carts may be more carefully tended. One proposal for a mobile cart washing system is shown in Poitevin, U.S. Pat. No. 4,807, 319. However, this system has apparently not been commercially adopted, due it is thought by the fact that washing is a bottom-line pure cost item with no cost sharing or incentive to the grocery store to adopt.

Carts, of course, have become increasingly expensive. They generally fall into two categories, stainless steel, and plastic. While the stainless steel tend to be more expensive, they are projected to have a longer duty life.

In addition, carts are often used as a medium for in-store advertising by attaching promotional material to the cart. An effective cleaning operation will tend to remove paper or other disposable advertising materials from the cart. It is possible to use permanent advertising materials mounted to carts. However, popular "Cents-off" and other types of special deal coupons are in wide use in the grocery trade, and these prior-art coupons are not adapted to be permanently mounted to carts, are typically produced as disposable paper items and frequently reference time-limited or frequently changing promotional offers.

These coupons are normally delivered in a variety of ways, including packs of coupons which are mailed to occupants, or in magazines or newspaper run of press, or which may be on-pack or in-pack type coupons, or which may be printed on the backside of a cash register tape. The consumer must either clip out or otherwise separate the coupons, or they must sort and store coupons, and take them to the store. In the case of the register tape coupons, most are cross-sell deals, that is, coupons of merchants other than the vending merchant. They are received at the exit end of the shopping activity and are expected to be used on a subsequent visit. In turn, this requires the consumer to cut apart, sort and store coupons for future use. In some instances, there may be stacks of coupon-containing flyers or special coupon books available at the stores for use by consumers upon entering the stores. These are not handy and may be missed because of their special location, or too much effort is required by the consumer to obtain the coupon books. It is advantageous to provide such coupons to consumers mounted the cart used by the consumer within the store, since this presents the coupons to the consumer's view immediately upon entry to the store, and serves to hold the coupons in readiness as the consumer shops.

There is a need in the art for an effective and economical method and automated system for preparing carts for consumer use, including cleaning, disinfecting and drying of the carts, to present a hygienic and pleasing cart to the consumer and which provides a cost incentive to the store to adopt the cleaning system. There is also a need for a system and special type of coupon that will ensure a very high percentage, on the order of 80–90%, of all consumers entering a grocery store will receive the coupons, and which are easy to manage and can be used during the shopping trip. There is also a need for a system that permits rapid change of coupons, shorter lead time for planning, and special occasion coupons.

DISCLOSURE OF INVENTION

SUMMARY, OBJECTS AND ADVANTAGES

It is an object and advantage of this invention to provide apparatus and methods (herein "systems") for cleaning and treating grocery-type "purchase item" carts via a modular unit that can be installed at the store, and which functions either manually or automatically in a continuous or batch mode. It is another object and advantage of this invention to provide a system for cleaning and disinfecting grocery carts on an as-needed or scheduled basis, as often as after every use, so that the cart is presented to the consumer in a treated, clean condition, and which includes store-adoption incentive system, namely consumer coupons.

It is another object and advantage of this invention to provide a system and apparatus for providing customers entering a grocery store a special type of "hot", rapid change, short lead time, special occasion type coupons that can be used during the same shopping trip, and that are readily accessible and easy to manage by the consumer. It is another object and advantage of the invention to provide a method and apparatus for applying a strip containing at least one promotional coupon to the handle of a grocery cart so that the consumer, upon entering the grocery store will have ready access to the coupon.

It is another object of the invention to provide an apparatus for automatically applying strips of coupons to grocery cart handles for easy availability by the consumer upon obtaining a grocery cart. It is another object and advantage of the invention to provide a special type of grocery coupon on a strip attached to a grocery cart handle which permits the coupon to be visible and easily accessible. It is another object and advantage to provide an improved coupon system in which multiple coupons are applied as part of a strip to a grocery cart handle, with successive coupons being separable from the strip by transverse perforations or score lines in the strip. Still other objects and advantages will be evident from the description, drawings and claims of this application.

The invention comprises both apparatus and methods for continuous and/or batch treatment of purchase item carts, commonly known as grocery type carts, whether they are used in grocery stores or other types of retail establishments. The system comprises a generally tunnel-like housing within which at least one, but preferably a plurality of treatment stations are disposed, and preferably includes either an automatic, motorized pull-through or pusher type of cart movement apparatus, or provision for guided manual push-through of carts.

The treatment system of the invention comprises one or more of a pre-wash, washing disinfecting, rinsing, stripping and drying zones. The invention also comprises a method and apparatus for applying a strip of specially adapted grocery coupons to a handle of a grocery cart comprises a leader portion and a coupon portion.

The pre-wash and wash zones are typically high pressure spray heads, with or without rotary brushes, for removing soluble foreign materials from the cart. Where the foreign materials are light or the cart is simply dusty, one or the other of the two pre-wash or wash stages can be omitted. That is, the cart chassis can be run through the pre-wash stage and then go directly to disinfecting, or it can be run through the wash stage without pre-wash followed by the disinfecting stage. In addition, in one important alternative, the system comprises a continuous (sequential multi-manifold) or batch (single manifold) washing and disinfecting station(s) , with pre-washing simply being done by the carts being hosed off prior to being introduced into the system tunnel, and post-cleaning drying is air drying outside the unit.

Following the drying stage, a strip of specially adapted grocery coupons is applied to a handle of a grocery cart, in part as a key incentive to the store to adopt the washing system. The coupon strip comprises a leader portion and a coupon portion. The leader can be wrapped around the handle over the grocery cart manually or by means of the automated machinery described in this application. The coupon strip portion may contain at least one coupon. Where multiple coupons are attached to the strip, they may be separated from the strip by transverse perforations or score lines.

These coupons serve as a double incentive—They are a real-time consumer coupon delivery system, and function as a cost-recovery mechanism for the store which is an incentive to the store to adopt the washing/cleaning system. The store can recover some costs by coupon distribution fees to manufacturer-sponsors of the coupons. Included in the term "coupons" as used herein, are other types of advertising, such as local ads currently printed on the back of cash register tapes.

In the preferred embodiment, the apparatus of the system invention comprises an external housing on the order of 4' high 3' wide and from 6'–25' in length, depending on the number of treatment stations (manifolds) within the housing and the needed capacity, measured as carts per hour throughout. The unit may sit directly onto concrete or asphalt, in which case there will be one or more floor drains. In the alternative, it can be mounted on a base which contains drains, fluids distribution piping, and a cart towing or pushing mechanism. This movement or shuttle mechanism is typically a moving chain to which are attached vertical pusher arms that extend upward to catch the cart to draw it through the enclosure while being treated. In the alternative, the cart towing or pushing mechanism can be located in one or both sidewalls, and can engage the cart in any convenient place, such as the tubular frame at the front, sides or back, or the basket mechanism itself.

This movement mechanism will herein be described as a "towing mechanism" regardless of whether the carts are pulled or pushed through the washing/treating units. By "disinfecting" is meant reduction in microbial contamination, and may include sanitizing selected cart surfaces.

As noted above, however, no towing mechanism is absolutely required, as an attendant can push the carts through the tunnel, either one-by-one or in nested groups. Prior to being introduced into the washing/treatment unit, the attendant removes any paper or other non-soluble materials that may be left in the carts, and also removes any child seats. Depending on the spray head configuration, and whether the carts are individually propelled through the unit or are nested, the standard retractable shelf (which has a moveable plastic flap, permitting use either as a child seat or as a shelf) is either deployed in its use position, or retracted substantially vertically against the back of the cart. The carts, either singly or in the nested groups are propelled through the washing/treating tunnel where they come to a first of a plurality of stations. As noted above, in a first embodiment the first station is a pre-wash station wherein pressurized water, which optionally may be heated, is delivered in distributed sprays to wash off major accumulations of dust, dirt, food or other material.

The cart then continues to a second, washing station wherein a high pressure ambient or (preferably) heated water and detergent formulation is used to thoroughly pressure-wash the surfaces of the cart through an array of high pressure fluid delivery nozzles positioned to access the key surfaces of the cart.

Then, the cart moves forward to a third, disinfecting station wherein a disinfectant solution is sprayed on the cart in controlled amounts. A convenient spray solution is chlorinated water comprising a concentrated hypochlorite solution diluted in water. The resultant disinfectant solution may range in temperature from ambient to warm, although ambient temperature is preferred in order to maintain the chlorine in solution. Warm water, while it activates chlorine, also causes it to de-gas from the water, thus reducing its overall effectiveness. The amount of chlorine, provided as hypochlorite to the water, is sufficient to insure a preselected level of disinfection. Typically this can be obtained when approximately fifty parts per million chloride/chlorite (conveniently measured as free chlorine) remain in the run-off after treatment of the cart. This is deemed adequate to insure effective disinfecting of the cart surfaces.

Thereafter, and in the best mode preferred embodiment, the cart can proceed to an optional fourth station in which forced air is provided to assist in stripping off excess water. If desired, the air can be heated and of sufficient quantity and duration to completely dry the cart, although that is not a requirement of the process of the invention. In the preferred embodiment, the carts can exit to a waiting station wherein they dry under ambient conditions either indoors or outdoors.

In an equally preferred embodiment, the number of stations can be adjusted so that there are more washing or disinfecting treatment stations, or less. For example, where there is a only very light soiling of the carts, the pre-wash station and step can be eliminated. Conversely, where needed, the washing station can be eliminated. Thus, the minimum can be one pre-washing or washing station and one disinfecting station, with one or no forced air stripping or drying station. In an alternative to a forced air or drying station, radiant heat can be used to promote evaporative drying. This embodiment would be most appropriate for stainless steel carts to avoid heat or radiant energy damage to the plastic carts.

In the batch mode the carts are pushed into a single treatment zone, and the different fluids (pre-wash water, aqueous detergent solution, rinse water, disinfectant solution, rinse water, blown ambient or heated air) are sequentially cycled through the pipe manifold and spray head and air ducts.

The optional incentive coupon application to the cart follows the drying phase. Applying coupons is considered the present best mode of the system and method of the invention. In continuous operation, the coupons may be applied at a station integrated with the cleaning system, with the carts preferably being moved or towed directly to a coupon application zone. In batch processing, the carts will generally be moved as a batch to a coupon applying station. The term "coupon" is used herein most generally to include a strip of paper or other sheet material being applied to the handle or other rod-like portion of the cart body, such as the cart lip member inboard of the handle. In preferred embodiments described below, paper strip coupons are applied to the handle of the cart, although plastic or other sheet materials can be used.

The coupon strip in a first embodiment can be carried on a continuous carrier web or strip of paper from which the coupon strips can be sequentially peeled off and applied to the grocery cart handle by the automated apparatus disclosed in this application. The peel-off coupon strip can include a transverse strip of pressure sensitive glue at one end of the leader so that when it is rolled around the handle, it can engage the back side of the leader forming a loop. Optionally, the leader can also include a strip of pressure sensitive glue spaced some 3 to 6 inches from one end so that when the coupon strips (with leader) is peeled off the carrier web, it can be temporarily affixed to the top of the handle until the cart moves to the second position where a pair of rollers, preferably sponge rollers, can roll the leading edge of the leader around the handle to engage the other end of the leader forming a loop to which the coupons are affixed or extend.

The couponing apparatus comprises two subsystems, a first, coupon/leader applying assembly, and a second, wrapping assembly for rolling the leader around the handle for securement to itself in a loop so that the coupons extend downwardly from the loop. The individual coupons, being separable from each other by score lines or microperforations, can be removed easily by folding along the transverse perforated score lines and then torn off for redemption. Since the coupons simply hang down in a strip, they can be easily consulted as the consumer is pushing his/her cart into and through the store.

The wrapping apparatus assembly can take a variety of forms, with the presently preferred being a pair of spaced, foam or pad-type rollers having axes which are parallel to the axis of the grocery cart handle. In the raised position, the rollers are biased together. Upon vertical, downward reciprocation of the two rollers, one at each end of a Y-shaped vertically movable actuator, they roll the leader around the handle. Being spring biased together, they then close after they pass around the handle and cause the glued end of the leader to come in contact with the other end of the leader thus securing it into a loop around the handle. After vertical upward return of the paired rollers, the leader is effectively wrapped around the handle. Any other suitable conventional wrapping mechanism may be employed.

The coupon and leader strip can be in multiple parts, for example, two parts form the loop and a separate part forms the coupon strip. The material of the leader is easily frangible so that it can be removed and disposed after the consumer has separated whatever number of coupons he/she desires to use or keep.

BRIEF DESCRIPTION OF DRAWINGS

The invention is described in connection with the drawings in which:

FIGS. 4A, B shows a grocery cart with the coupon and leader of this invention applied thereto by the apparatus of this invention, FIG. 4A being an isometric view and FIG. 4B detail side view of the coupon leader on the cart handle; and FIGS. 5A–D are a multi-part schematic of the apparatus and process for applying the coupon and leader promotional device of FIG. 4A, FIG. 5A showing the cart handle approaching the station, FIG. 5B showing tacking the coupon strip to the handle, FIG. 5C showing the coupon and leader tack-glued to the cart handle, and FIG. 5D showing the leader sealed to the back of the coupon to form a loop.

DETAILED DESCRIPTION OF THE BEST
MODE OF CARRYING OUT THE INVENTION

The following detailed description illustrates the invention by way of example, not by way of limitation of the principles of the invention. This description will clearly enable one skilled in the art to make and use the invention, and describes several embodiments, adaptations, variations, alternatives and uses of the invention, including what is presently believed to be the best mode of carrying out the invention.

In this regard, the invention is illustrated in the several figures, and is of sufficient complexity that the many parts, interrelationships, and sub-combinations thereof simply cannot be fully illustrated in a single patent-type drawing. For clarity and conciseness, several of the drawings show in schematic, or omit, parts that are not essential in that drawing to a description of a particular feature, aspect or principle of the invention being disclosed. Thus, the best mode embodiment of one feature may be shown in one drawing, and the best mode of another feature will be called out in another drawing.

Figure 1:
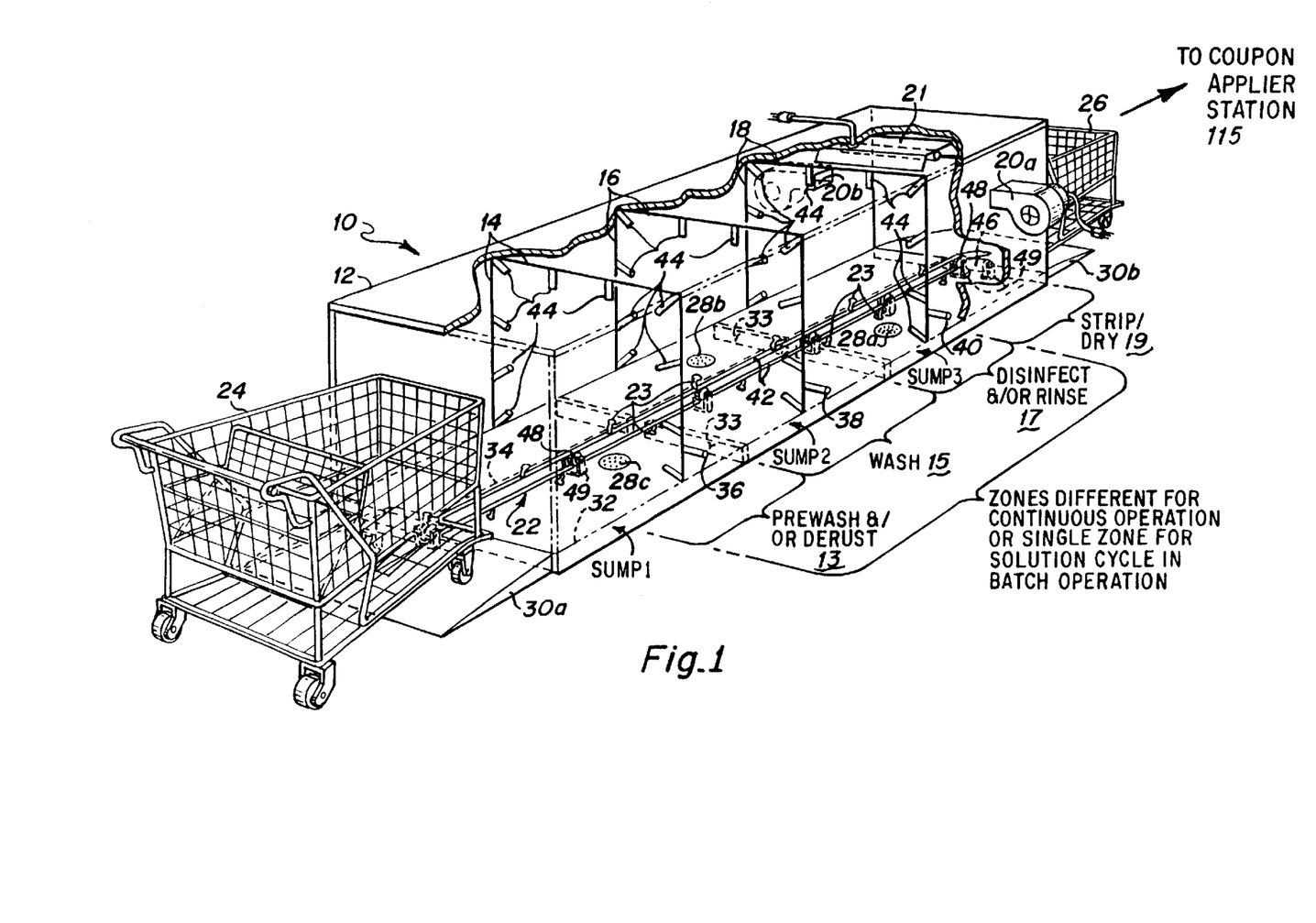
FIG. 1 is an isometric view, partly schematic, of an embodiment of the cart washing/disinfecting apparatus of the cart treatment-coupon application system of this invention.

FIG. 1 is an isometric view of the washing/disinfecting system 10, which comprises a housing 12 having therein a plurality of zones, including a first, pre-wash zone 13, a washing zone 15, a disinfecting and/or rinse zone 17 and an optional drying zone 19. Disposed within the housing in the pre-wash zone 13 is a fluid manifold 14 comprising a pipe system having plurality of nozzles as shown, and an exterior connector or union 36 to which a water pipe or hose is connected (not shown). The interior water distribution line or piping manifold 14 is shown as a single line in order to not clutter the drawing. The nozzles 44 are shown schematically due to the scale of drawing, but they are any conventional spray nozzle, preferably a commercially available plastic spray nozzle such as a Delrin tee jet. As shown in the figure, there are four nozzles vertically arrayed on each side and two additional ones spaced uniformly across the top. The bottom two nozzles may be angled somewhat upwardly to achieve good coverage of the underneath of the cart structures, whereas the upper two along the side walls are angled somewhat laterally and downwardly to obtain good coverage of the basket internals. The top two can also be angled somewhat forwardly (to the right in FIG. 1) or rearwardly (shown to the left in the FIG. 1) in order to fully contact the front and rear interior sidewalks of the cart, respectively. Note that the pre-wash zone is recessed somewhat inwardly of the entry (left) edge of the tunnel-like housing so that the spray is confined to the internal zone. Relatively narrow plastic strips can be suspended from the top rear (left) edge of the tunnel in order to provide additional spray block. They are not shown in the drawing due to scale and in order to not obscure other important features of the invention. The cart 24 is introduced into the tunnel as shown. The front lower cross bar of the cart chassis can be engaged by fingers 23 attached to the power driven chain tow mechanism 22. The tow mechanism 22 which comprises drive motor 46 driving sprocket 48 which in turn engages tow chain 42, the fingers 23 being mounted to chain 42 projecting outward, so as to project upward through slot 34 in floor 32 from the upper portion of the chain loop 42. The fingers 23 progressively tow the cart 24, 26 through the tunnel as the chain 42 moves.

A second piping manifold 16 is disposed within the wash zone 15, and includes at least one exterior inlet bibb or union 38 to which is connected a pipe or hose for delivery of wash water or wash solution. A preferred wash solution is warm or hot water containing an appropriate quantity of detergent, the amount of which can be readily determined through practice. Again, spray nozzles are disposed in a suitable array within the zone. Disinfecting and/or rinse zone 17 includes a piping manifold 18 connected through the exterior of the housing with bibb or union 40 to which an appropriate supply of disinfecting solution is provided under pressure. A convenient disinfecting solution is aqueous solution of hypochlorite in water, to provide on the order of from about 50 ppm to 500 ppm free chlorine in the solution. Ambient (50 to 80° F.) temperature water is preferred. A rinse zone may be employed either just upstream or downstream of the disinfecting zone 17. Ordinarily, rinsing after disinfecting is not required, but may be used if desired after washing to remove any soap solution.

In an important procedural option, a batch process may be employed. In this alternative embodiment, all zones are universal zones, and the carts are stationary during a treatment cycle. The minimum is a single zone. A fluid delivery manifold is attached to the inlets 36, 38, 40. Pre-wash, wash, rinse and disinfecting solutions are pumped in timed sequence series to all manifolds, and applied to the carts. Optionally, the manifolds can oscillate back and forth parallel to the cart path for good coverage. Or the carts can oscillate back and forth under fixed sprays. Where each zone has multiple piping manifolds, oscillation is not needed.

While a single, inverted U-shaped piping manifold is shown in each of the pre-wash wash and disinfecting zones, it should be understood that any multiple or branched line configuration can be employed with more or less nozzles angled in appropriate directions.

Further down stream from the disinfecting zone 17 is a stripping and/or drying zone 19 which conveniently may have one or more blowers 20A, 20B disposed to provide ambient or heated air to the wet cart to strip the excess water and/or solution therefrom and/or to dry it. In an important alternative, a radiant heater 21, such as any commercially available infra-red radiant heater, can be provided near the exit of the tunnel 12 to speed and improve drying, particularly to the interior surfaces of the cart. The now clean carts 26 exit the tunnel where they are moved to a customer availability area, or preferably to the coupon application system of FIGS. 4–5D. In one embodiment, the right hand end of the tunnel (the output end exiting the coupon application station) can be flush to an aperture in the store perimeter wall through which the carts are ordinarily pushed so that customers can take freshly washed carts with coupons applied as they enter the store. In the alternative, the entire tunnel apparatus (including the optional coupon applier) can be at some distance from a customer receiving area, and the carts pushed by hand from the exit end of the tunnel to the cart receiving or waiting area.

In another important alternative, a floor 32, which may be ground level or raised, is provided in the tunnel with a slot 34, through which the fingers 23 project upwardly. This floor can conveniently be any type of grate such as a X-Met type grating. A flat sheet metal trackway can be provided for the cart wheels. These trackways can have vertical flanges on the inside and outside to provide a positive guideway for the cart wheels so that the carts do not become jammed cross ways during transit through the tunnel. Note also entrance ramp 30A at the entry end and exit ramp 30B at the exit end of the tunnel. In addition, one or more floor drains 28A, 28B may be provided.

In the alternative, where the unit needs to be totally self enclosed such as an interior unit or where required by code, the space between the floor and the bottom edge of tunnel can provide a sealed sump which can be drained by any suitable pump mechanism. In that embodiment, transverse portions separate the disinfecting zone from the pre-wash and/or wash zone in order that the chemical compositions of the different fluids do not mix. The use of the fluids can thus be progressive. That is, recovered pre-wash zone water can be cycled as makeup water to the wash zone or vice versa depending on the soil and biologicals load of the drain water. Typically the disinfectant zone solution will be kept separate for appropriate recycle use until exhausted, as measured by the drop in parts per million of chlorine to below about 50 ppm. In a steady state condition, there will be continuous withdrawal of a portion of the solution to drain, plus new solution make up in order to keep proper solution concentration.

Following the completion of the drying stage, the clean cart 26 is released by the finger 23 and exits the washing/disinfection tunnel 10 towards the optional coupon applier apparatus 115 (see FIGS. 4 and 5 below), which may optionally be integrated with the washing/disinfection tunnel 10 and the chain 22 extended, so that coupons are applied before the cart 26 is released from tow chain 22.

Note that although FIG. 1 shows the washing/disinfection (and optionally coupon application) system 10 as a floor mounted unit, the system 10 may also be a mobile unit, preferably mounted to the bed of a truck or trailer, thus permitting a single system to conveniently service carts at a number of supermarkets or stores. Power, water and drainage may be provided on-vehicle, or a connection to water, power or sewage can be provided at the drive-up site.

Figure 2:
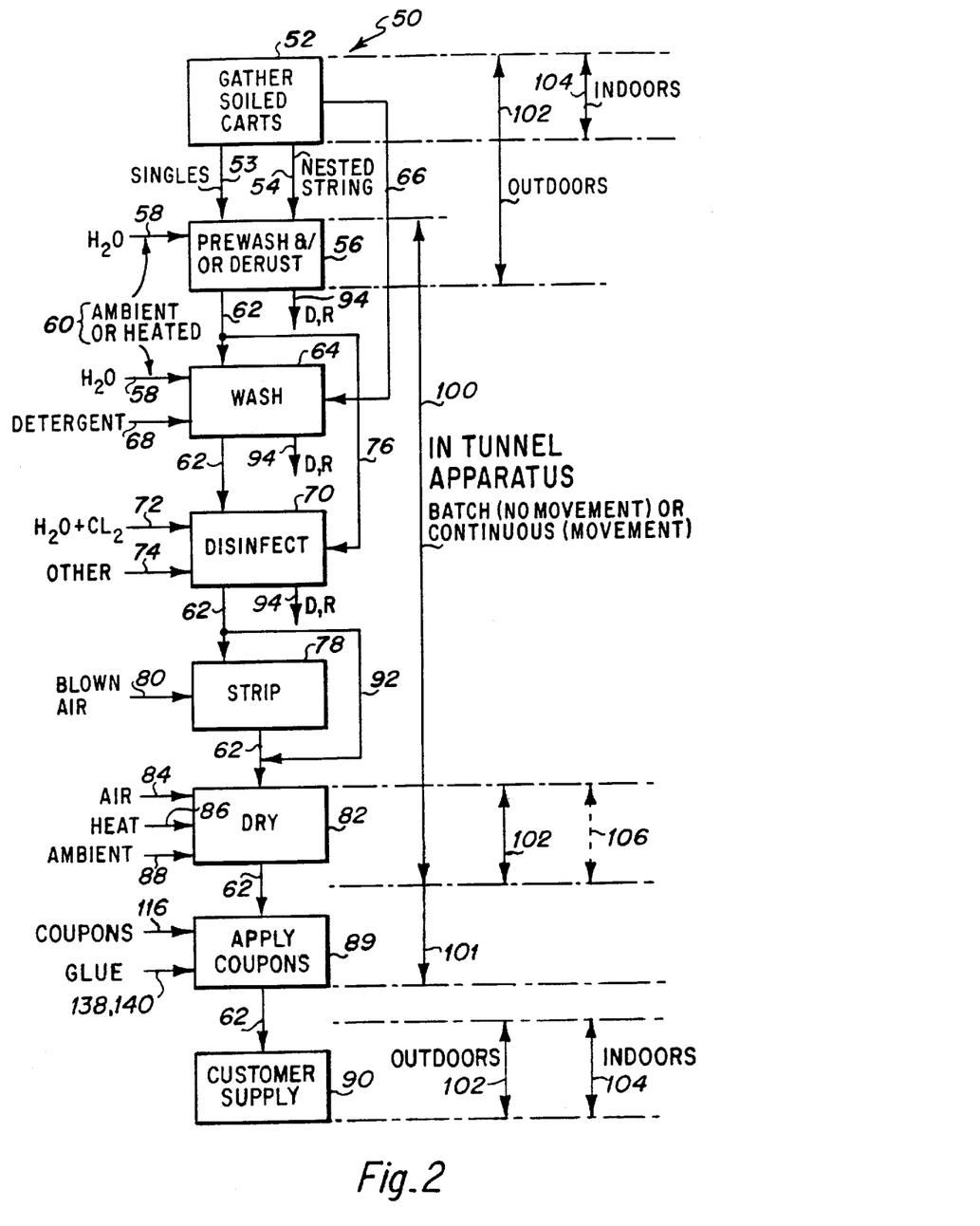
FIG. 2 is a schematic flow sheet showing the various alternative processes of cart treatment and coupon attachment of this invention.

FIG. 2 is a schematic of the several alternative processes of this invention. On the left side is the flow sheet, and on the right side are a series of lines which show the location wherein the process steps take place.

Note that this process covers either a batch process (in which case cart movement 62 between zones is eliminated), or a tunnel system having multiple dedicated treatment zones. The soiled carts are gathered 52 and, either as singles 53 or as nested strings 54, are forwarded to the treatment unit of FIG. 1 where they are introduced into the pre-wash zone 56. There, water 58 is introduced to remove some of the dirt or other solubles. The rinsed carts are forwarded at 62 (except in a batch process) to the wash zone 64 wherein water 58 or/and detergent 68 solution is used to wash the carts. As shown by bypass line 66, the soiled carts can enter directly into the wash station 64. Exiting the wash station at 62, the washed carts move (except not in a batch process) to the disinfectant station 70. As shown by bypass line 76, the pre-wash carts may skip the wash section entirely where the pre-wash has removed any light accumulations of dust but there are no major accumulations requiring more thorough washing. In the disinfecting zone 70, chlorinated water 72 or other suitable disinfectant solution 74 is introduced to wet down, at least the interior basket and the handle portion of the cart.

The thus-treated carts are moved at 62 to a stripping zone 78 where in air is input via a blower (such as a blow-off jet or curtain stripper) or a suction device (such as a Vortec brand transvector air amplifier) to strip off the major accumulations of water. The damp carts are moved at 62 to a drying zone 82 wherein air 84 is blown across the carts to dry them. In the alternative, the air may be heated or they may be radiant heat dried, 86. In still another embodiment, the carts can merely be let dry at ambient temperature. From this zone, the clean carts 62 are then returned to the customer supply marshaling area. As noted by bypass line 92, the stripping zone may be bypassed and the carts can go directly from disinfecting zone 70 to drying zone 82. Alternately, the carts can be rinsed with fresh water after disinfecting, but this is not preferred.

As noted at 60, the water in the pre-wash zone and washing zone may be either ambient water or heated. The water introduced in the disinfecting zone is preferably at ambient temperature since it contains chlorine, as hypochlorite. In each of the pre-wash, wash, rinse and disinfecting zones, the run off water or solution 94 may go directly to drain or be recycled ("D,R" in FIG. 2).

To the right of this flow chart is a first line 100 which shows that the steps of pre-washing through drying may occur in the tunnel apparatus 10 of FIG. 1 as a batch or continuous process. Following drying, the optional coupon application step 89 may be included, taking place adjacent the coupon applier apparatus (see FIGS. 4 and 5 below). As indicated by line 101, the coupon applier may be installed indoors as a separate fixed station, may be a portable unit, or may be optionally integrated with the washer/disinfection system so that coupons are applied before the cart leaves the tow chain.

In the alternative, the soiled carts may be gathered and pre-washed outdoors as shown by line 102. In certain types of stores, or if desired or required, the carts may remain entirely indoors and never exit the retail facility; this is shown at 104. Likewise, the drying and customer cart supply marshaling area 90 can occur outdoors, as shown by the lower line 102. The customer supply marshaling area may also occur indoors at 104, and optionally the drying can occur indoors at 106.

The manifold piping may be any suitable pipe or other conduit such as high pressure water piping for the washing, Schedule 80 plastic piping for the pre-wash, and pressure hose for the disinfectant solution.

In the batch embodiment, a timer and valving system can be used, much as in a conventional dishwashing system. An electronic version permits programming for individual timer periods for each processing step (pre-wash, wash, disinfect, rinse, strip, dry) depending on needs, much as in a conventional sprinkler system. Predetermined sequences can be programmed in an EPROM by the manufacturer and the user can select by single-button keying of a keypad. An example could be 30 second pre-wash, 1 minute wash, 15 second disinfect, for a "Light" soil load, 50% more for "Medium" soiling and 2X for "Heavy" soiling. The keypad can have simple function keys for users, such as "Light" "Medium", "Heavy", for the different soiling conditions, which single button input initiates the respective preprogrammed timing sequences. The stripping and drying steps can take place in the same, single batch zone, or may take place in an adjacent zone with the carts moving from the multi-step first zone (pre-wash, wash, rinse, disinfection) into the stripping/drying zone. Where the carts stay in the same zone, movable dampers are used to seal off the blowers from the fluid spray.

It should be understood that the term "spray" as used herein includes introduction of a stream of solution onto the cart surfaces as it moves through the zones. Thus, appropriately angled and directed stream, jet, conical, air amplified spray, or fan type sprays can be employed in the various zones of the washing/disinfecting assembly.

The antimicrobial or disinfecting solution may be any FDA approved, food grade ingestible antimicrobial. It is presently preferred to use an aqueous solution of sodium hypochlorite, NaOCl. One source is conventional bleach. Optimally, a citrate-phosphate buffer mixed in water can be added to bring the pH in the range of from 6 to 7.5, preferably 6.5–7.0, and the free chlorine concentration to within the desired range of from about 50–500 ppm, preferably 80–300 ppm on the delivery side, but sufficient to leave about 50 ppm in the discharge. A convenient buffer that may be used is ORP buffer from Morgan Gallacher Inc., Santa Fe Springs, Calif. The hypochlorite may be "AgChlor 310", a 12.5% concentrated hypochlorite solution from Dacco Inc., a division of ELF Atochem. The pH should be kept above 5.5 as the hypochlorite degasses at a lower pH.

The flow rate of the chlorinated treatment fluid can be increased to compensate for a low chlorine content (concentration). Accordingly, the process includes maintaining a sufficient chlorine concentration and flow rate to provide free chlorine in the run off water at a particular cart throughput rate. As noted above, as the day progresses, the chlorine content in the spray water may need to be increased to compensate for environmental conditions. Typically, early in the morning there is low wind and it is cool. As the day heats up and dust builds up, the chlorine content may need to be adjusted upwardly.

Any commercially available spray or discharge nozzle may be used. Typical nozzles include Tee-Jet types 8004 and 107. Chlorinated water streams can be delivered at pressure, typically 20 psi, with the rate (gallonage) being adjusted to accommodate the number of carts treated per hour.

While disinfecting/antimicrobial treatment is preferred, it is not required, for example, where carts need to be cleaned but not sanitized, say at a home improvement or computer store. Further, the washing can be plain water, preferably hot plain water. The movement of carts is relative with respect to the treatment unit. The carts can be stationary and the unit moved, e. g. on tracks or wheels. The unit can have doors at one or both ends, for not-in-use security and for batch processing carts. The housing can be omitted where not needed, or only certain zones covered, e.g. the disinfecting zone. Each zone can be a self-contained module so that full units can be custom designed and/or zones can be pulled out and serviced or replaced. Thus, a full line can comprise: an entry module (tunnel housing 3'-6' long with a door at one end) ; a pre-wash module; one or more wash modules; one or more rinse modules (same as pre-wash); a disinfecting module, a water stripping module; a drying module; a discharge module (like the entry module).

Figure 3:
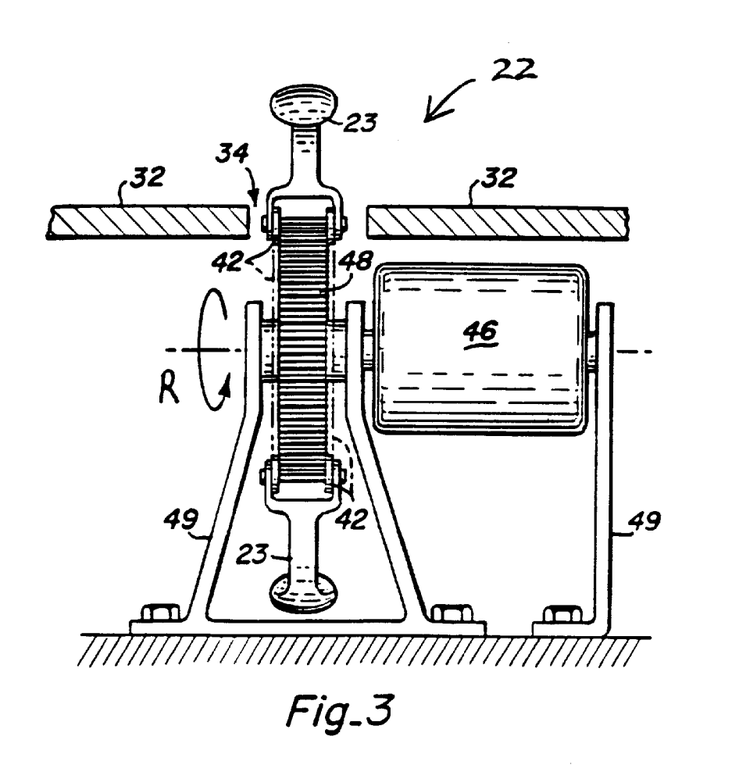
FIG. 3 is a front view of the cart tow chain drive mechanism.

FIG. 3 is a front elevation view of the cart tow mechanism 22 comprising drive motor 46 mounted to drive the chain 42 and sprocket 48 for cart towing. The stand 49 fixedly supports motor 46 located below floor 32. The stand 49 also pivotally supports sprocket 48 which is mounted to and driven by motor 46 as shown. Sprocket 48 is oriented in a vertical plane aligned with slot 34 in floor 32, so that the upper portion of sprocket 48 is adjacent slot 34. Chain 42 engages and is driven by sprocket 48, and mounts the plurality of fingers 23 spaced along the chain loop. The fingers 23 of the upper portion of chain 42 projecting outward from the chain through slot 34 and are in position to engage the lower portion of the body of the cart 24, 26 as the chain moves, thus towing the cart. The motor shaft and sprocket rotate as shown by Arrow R so that the upper portion of chain 22 moves forward along the axis of tunnel (10 in FIG. 1).

Figures 4A, 4B, 5A, 5B, 5C, 5D:
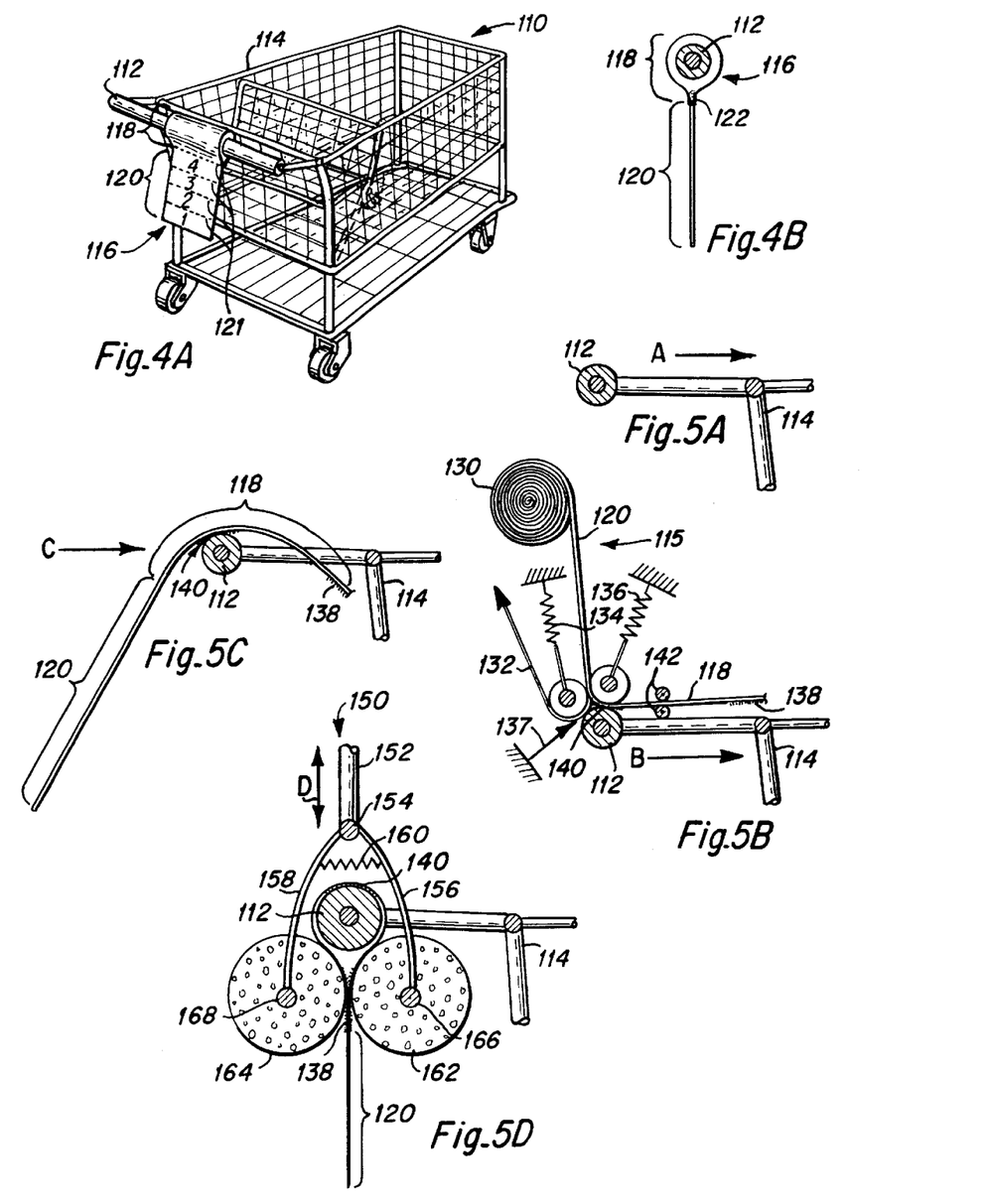

FIG. 4A shows a grocery cart 110 with a standard handle 112 which is spaced the usual distance from the cart body 114. A promotional coupon 116 is shown attached surrounding the handle 112. The cart is of the usual construction, of which there are a number of variations, including an optional folding seat for infants, the materials of construction such as stainless steel, plastic coated steel, plastic or composite materials. Likewise, the carts vary considerably in size from the giant carts used in discount and club-type stores (e.g., Costco, Home Depot) or mini-carts that are used in smaller stores.

The promotional device 116 of this invention is shown in side view in FIG. 4B. mounted around handle 112, shown in cross-section. It comprises a leader portion 118 and a coupon portion 120. The leader portion is shown in FIGS. 4A and B to be wrapped around the handle and secured to itself at point 122, much as an airline routing tag for luggage. The coupon portion 120 may be subdivided longitudinally into a one or more tear-off sub-portions by perforation lines 121 (four are shown, numbered 1–4).

FIG. 5A–D illustrates in four schematic sub-parts both the method and apparatus for applying the promotional coupon device 116 of the invention to the handle 112. Preferably the coupon applying and wrapping stations 115, 128 of this invention are integrated with the washing, disinfection and drying apparatus and follow the drying station 19 shown in FIGS. 1 and 2.

The grocery cart 114 having handle 112 is shown in FIG. 5A moving to the right as designated by Arrow A. entering coupon application station 115. Once in the coupon-applying station as shown in FIG. 5B, a roll 130 of coupons 116 to be applied are releasably carried on the surface of peel-off carrier web 132 which descends downwardly and between spring-loaded roller assemblies 134 and 136. As seen, the direction of carrier web 132 is reversed around roller assembly 134 so the coupon leader 118 can be peeled off by blade 137 and adhered with pressure-sensitive glue 140 at its midpoint to the top of the handle 112. The leader portion 118 extends forwardly, optionally maintained in an appropriate position by rollers 142. This occurs as the cart continues to move as shown by Arrow B. The result of the intermediate adhering or "tack gluing" of the coupon device 116 to the handle is shown in FIG. 5C. There, it can be seen that the leader section is lightly adhered at its mid-point by pressure-sensitive "tack" glue (also caled "PS glue") or adhesive 140 to the handle 112. Note the fixing glue 138 on the forward lower side of the leader section 118. The coupon section 120 already dangles downwardly behind the cart handle 112 as the cart is moved towards the wrapping apparatus as shown by Arrow C.

FIG. 5D shows the wrapping apparatus 128. There, a reciprocating wrapping mechanism 150 vertically reciprocates as shown by Arrow D to wrap the leader 118 around the handle of the cart 112 resulting in the mounted assembly as shown in FIGS. 3A and 3B. The reciprocating wrapping mechanism 150 comprises a powered, vertically reciprocating arm 152 having a pivot 154 in its lower end from which are arcuately pivoted a pair of opposed arms 156 and 158, on the ends of which are mounted resilient foam rollers 162, 164 on shafts 166, 168, respectively. Both rollers are urged together in contact or near contact by spring 160 which provides a pressure biasing the rollers together. As the cart handle 112 passes under the reciprocating wrapping mechanism 150, the arm 152 descends, the rollers roll around the handle 112 at the same time wrapping the leader section 118 around on itself so that the pressure sensitive "fixing" glue or adhesive 138 is adhered by pressure to the back side of the leader just above the coupon section 120, as shown. The portions of applying station 115 and wrapping station 128 not shown and their respective mountings are conventional. One of ordinary skill in the art will be able to make and use the coupon applying apparatus of the invention, with reference to the specifications and drawings herein.

Industrial Applicability

It is evident that the system of this invention has wide industrial applicability, not only to grocery stores, but also to any retail or wholesale store that employs carts. In addition the unit can be mounted on a truck or trailer bed to be portable for a service route type business, particularly to service small stores that cannot afford, or due to volume does not need, the full system. Such a unit would include the floor, plenum and sump system to be completely contained as a portable unit. Stores will receive excellent image ratings by having clean, sanitized carts presented to customers as they enter the store, and have costs at least partly covered by coupon distribution revenue.

The system apparatus and method of this invention also have wide industrial applicability to the delivery of promotional coupons to grocery cart handles. The couponing industry is both broad and vital to retail operations, and the system of this invention provides a uniquely new way to deliver hot coupons to consumers at a time and in a manner in which they will be most useful to the consumer and most likely to have the offer acted on, and the product introduced to, the consumer.

A printer can be mounted at the point of feed of the coupon stock so that real-time changes in coupon offers can be made. The coupon stock can be roll stock, fan fold or sheet. The printer can be computer driven so that the coupon offers can be updated or modified, such a by changes in expiration date, value, sponsor, product, or the like. Changes can either be entered at the store, or for computer driven printers, linked via means such as the Internet, wireless or WAN to a remote control/management center.

The reciprocating wrapping apparatus can be employed in a wide variety of other industries, wherever labels, tags or notices need to be applied to any type of bar or rod. It should be understood that various modifications within the scope of this invention can be made by one of ordinary skill in the art without departing from the spirit thereof. For example, the unit can have the capability of operating in either a batch or continuous mode, with all the multiple manifolds being alternately selectable to cycle a sequence of fluids in the batch mode. It is therefore wished that the invention be defined by the scope of the appended claims as broadly as the prior art will permit, and in view of the specification if need be.

What is claimed is:

1. A method of delivery of redeemable promotional offers on the handles of shopping carts provided to consumers comprising the steps of:
    a) providing at least one preselected, consumer promotional offer comprising paper sheet material including thereon preprinted information relating thereto that includes at least one redeemable coupon offer; and
    b) providing an automated applying station for automatically applying and physically temporarily attaching said paper sheet material, including said preprinted promotional offer, directly onto a limited portion of the handle end of an empty shopping cart prior to consumer use;
    c) so that the consumer, upon obtaining an empty shopping cart at a store receives said preselected promotional offer already attached on the cart for easy removal by the customer for immediate use and redemption by the customer.

2. Method as in claim 1 wherein said step of applying includes attaching said sheet material with an adhesive to a handle of a shopping cart.

3. Method as in claim 1 wherein said step of applying said sheet material includes securing a leader portion of said sheet material to said cart handle.

4. Method as in claim 1 wherein said step of applying is located at a store.

5. Method as in claim 1 which includes the step of printing coupons on said sheet material prior to said step of applying.

6. Method as in claim 5 wherein said printing is computer driven.

7. Method as in claim 6 which includes controlling said printing to provide changes in coupon offers.

8. Method as in claim 7 wherein said changes are computer controlled.

9. Method as in claim 8 wherein said computer is located at a store where said sheet material applying occurs.

10. Method as in claim 9 which includes the step of initiating coupon offer changes at said store.

11. Method as in claim 8 wherein said computer is located remotely from a store where said step of applying said sheet material containing said coupon offer takes place.

12. Method as in claim 11 wherein said computer driven printer is linked to a remotely located control/management center.

13. Method as in claim 12 wherein said link includes at least one of Internet wireless, LAN and WAN communication.

14. Method as in claim 13 which includes making coupon offer changes from said control/management center via said link.

15. Method as in claim 11 which includes the step of initiating coupon offer changes at said computer.

16. Method as in claim 15 wherein said step of coupon offer changes is initiated from a remotely located control/management center.

17. Method as in claim 16 wherein said coupon offer changes are made substantially in real time.

18. An apparatus for providing promotional offers on the handles of store shopping carts provided for presentation to customers comprising in operative combination:
    a) at least one automatic feeder that feeds paper sheet material associated with a promotion to a sheet material applying station; and
    b) an applying station receiving sheet material from said automatic feeder, said applying station physically temporarily attaches said paper sheet promotion material directly onto a limited portion of the handle end of a shopping cart prior to presentation to and removal by a customer for redemption of said promotional offer at said store.

19. An apparatus as in claim 18 wherein said promotion material includes at least one promotional coupon.

20. An apparatus as in claim 19 wherein said applying station attaches said sheet material to a shopping cart handle with glue.

21. An apparatus as in claim 19 wherein said sheet material is wrapped around said handle and secured to itself.

22. An apparatus as in claim 18 which includes a printer mounted in association with said sheet material automatic feeder to print offers in coupon form on said sheet material prior to applying said sheet material to said shopping cart.

23. An apparatus as in claim 22 includes a computer to drive said printer.

24. An apparatus as in claim 23 wherein said computer is located remote from said printer.

25. An apparatus as in claim 24 wherein said computer is located in a control/management center for making coupon offer changes.

26. An apparatus as in claim 18 wherein said applying station is mounted on a movable platform as a mobile station.

27. An apparatus as in claim 26 wherein said movable platform is a shopping cart treatment apparatus system, and said applying station attaches said sheet material to the handle of shopping carts after treatment.

28. An apparatus as in claim 18 wherein said applying station is disposed downstream of a cart treatment apparatus system and said applying station attaches said sheet material to the handle of shopping carts after treatment.

29. An apparatus as in claim 18 wherein said applying station includes a reciprocatable arm for attaching said promotion material to said shopping cart with glue.

30. An apparatus as in claim 29 wherein said shopping cart includes a handle, said material includes at least one area of pressure sensitive glue on a first side of said material and said applying station includes a pair of rollers spring biased together and mounted on arms from said reciprocatable arm so said rollers upon reciprocation roll said material around said handle so that said glue contacts the same side of the material securing the material to itself to form a loop of material around said handle.

\* \* \* \* \*

UNITED STATES PATENT AND TRADEMARK OFFICE
CERTIFICATE OF CORRECTION

PATENT NO. : 6,714,837 B1
DATED : March 30, 2004
INVENTOR(S) : Rogers F. Brackmann and Jacques M. Dulin

It is certified that error appears in the above-identified patent and that said Letters Patent is hereby corrected as shown below:

<u>Title page,</u>
Item [75], Inventors, should read:
-- Rogers F. Brackmann
  2014 Waverly Circle
  St. Charles, IL 60174

Jacques M. Dulin
  698 Oak View Place
  Sequim, WA 98382-3159 --

Signed and Sealed this

Twenty-second Day of June, 2004

JON W. DUDAS
*Acting Director of the United States Patent and Trademark Office*